United States Patent [19]

Nomura

[11] Patent Number: 5,447,726
[45] Date of Patent: Sep. 5, 1995

[54] ORALLY ADMINISTRABLE CHOLESTEROL LOWERING AGENT

[75] Inventor: Tatsuo Nomura, Ibaragi, Japan

[73] Assignee: Mitsubishi Kasei Corporation, Tokyo, Japan

[21] Appl. No.: 282,553

[22] Filed: Jul. 29, 1994

[30] Foreign Application Priority Data

Aug. 3, 1993 [JP] Japan .................. 5-192392

[51] Int. Cl.$^6$ .................. A61K 9/20
[52] U.S. Cl. .................. 424/464; 424/78.1; 424/78.14; 424/480
[58] Field of Search .................. 424/78.1, 78.14, 480, 424/464

[56] References Cited

U.S. PATENT DOCUMENTS 4,107,098  8/1978  Tamura et al. .................. 521/25
4,557,930  12/1985  Kihara et al. .................. 424/78.1

Primary Examiner—Gollamudi S. Kishore
Assistant Examiner—Pamela S. Webber
Attorney, Agent, or Firm—Wenderoth, Lind & Ponack

[57] ABSTRACT

There is provided an orally administrable cholesterol lowering agent which is obtained by coating with hydroxypropylmethylcellulose plain tablets containing an anion exchange resin as an active component and containing 14–20% by weight of water and not more than 2% by weight of silicon dioxide based on the weight of the anion exchange resin. The orally administrable cholesterol lowering agent is obtained by coating the above mentioned tablets with an aqueous solution of 10–30 cSt of hydroxypropylmethylcellulose. In addition to being characterized by easiness of swallowing, the orally administrable cholesterol lowering agent of the present invention is superior in compressing shapability, stability in a moistening environment, and fluidity.

13 Claims, 2 Drawing Sheets

ORALLY ADMINISTRABLE CHOLESTEROL LOWERING AGENT

BACKGROUND OF THE INVENTION

The present invention relates to an orally administrable cholesterol lowering agent and, more particularly, to an orally administrable cholesterol lowering agent which is superior in compressing shapability, stability under a moistening environment, and fluidity together with an easiness of swallowing.

Conventionally, anion exchange resins are large in dose and hence tablets become large. Considering swallowability, capsule-shaped tablets are preferable. For the capsule-shaped tablets, however, a part of a punch may be deformed upon compressing unlike circular tablets, and the punch is more likely to be broken. In methods of compressing with a certain volume of water contained that are conventionally made (Japanese Patent Application Laid-Open Nos. 2-286621 and 3-236326), a larger compressing pressure is required and are thus insufficient as methods of preparing plain tablets.

On the other hand, regarding the coating of tablets containing an anion exchange resin as an active component, such a method is known that uses cholestyramin resin and dissolves with heat stearic acid into polyethylene glycol for coating without using a solvent (Japanese Patent Application Laid-Open No. 3-236326). Tablets coated by this method are, however, inferior in storage stability in an open condition. The tablets are hygroscopically disintegrated in several hours at a room temperature. Accordingly, the tablets have only a poor stability after packaging is opened. In addition, a coating layer has a low strength and is greatly worn. The tablets may thus be broken in the packaging process or during transportation.

Commercially available cholestyramins are dry syrups dissolved on use and are desired to be formed into tablets considering the easiness of swallowing and handling. Favorable tablets have not been obtained yet because of the above mentioned reasons.

The present inventors have found a method for coating an anion exchange resin with hydroxypropylcellulose (Japanese Patent Application No. 4-320155). While the stability in a moistening environment of them is improved, the tablets coated by this method have, however, the disadvantage that the fluidity is lost with the tablets being adhered to each other because the hydroxypropylcellulose used as the coating layer absorbs water to increase the viscosity.

The present inventors had made tremendous studies and considerations with respect to the above mentfoned problems. As a result, it has been found that the compressing shapability can be improved significantly by using an anion exchange resin as an active component and containing, as secondary components a certain amount of water and silicon dioxide that is used as a fluidity imparting agent. It has also been found that such an orally administrable cholesterol lowering agent which is superior in easiness of swallowing, stability in a moistening environment, and maintenance of fluidity is obtained by coating plain tablets with hydroxypropylmethylcellulose having a higher viscosity than those commonly used.

SUMMARY OF THE INVENTION

According to an aspect of the present invention, there is provided an orally administrable cholesterol lowering agent obtained by coating with hydroxypropylmethylcellulose plain tablets containing an anion exchange resin as an active component and containing 14–20% by weight of water and not more than 2% by weight of silicon dioxide based on the weight of the anion exchange resin. There is also provided an orally administrable cholesterol lowering agent obtained by coating the plain tablet with an aqueous solution of 10–30 cSt of hydroxypropylmethylcellulose.

In addition, the present invention is directed to a method of preparing an orally administrable cholesterol lowering agent comprising the following steps.

Step 1: adding to an anion exchange resin 14–20% by weight of water based on the weight of the anion exchange resin while mixing, and then adding to the anion exchange resin not more than 2% by weight of silicon dioxide based on the weight of the anion exchange resin while mixing, and further pressing the mixture into plain tablets.

Step 2: coating the plain tablets with a coating solution which is an aqueous solution of 10–30 cSt of hydroxypropylmethylcellulose.

DETAILED DESCRIPTION OF THE INVENTION

Figure 1:
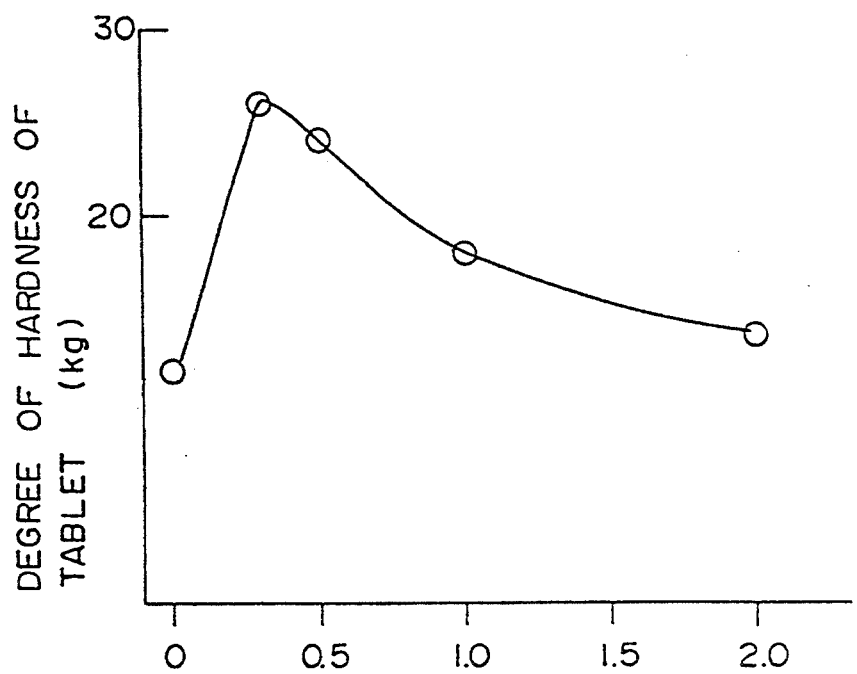
FIG. 1 illustrates a relationship between an amount of silicon dioxide added and a degree of hardness of the tablet.

In the present invention, the anion exchange resin used as an active component is not limited to a specific one as long as it lowers a blood cholesterol level. A preferable anion exchange resin is a 2-methylimidazole-epichlorohydrine copolymer obtained through a method disclosed in, for example, Japanese Patent Application Laid Open No. 60-209523. While having an irregular, complex stereo structure, the 2-methylimidazole-epichlorohydrine copolymer (hereinafter, also referred to as MCI-196) is represented by a basic structure of the following general formula (I), of which structure is partially represented by the following general formula (II):

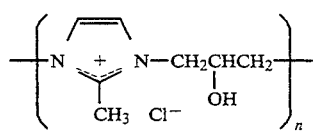

[I]

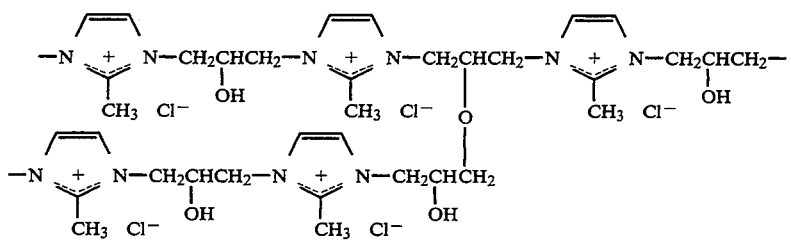

Water is added to this anion exchange resin such that 14–20% by weight, and preferably 15–19% by weight, of water based on the weight of the anion exchange resin is contained therein and is mixed therewith. In this event, a binding solution may be added along with water such as hydroxypropylcellulose. In addition, not more than 2% by weight, and preferably 0.2–1.0% by weight of silicon dioxide based on the weight of the anion exchange resin is added thereto and mixed therewith. The resultant mixture is then granulated by using a speed mill. A lubricant such as a hydrogenated oil is added thereto and mixed therewith, which is then subjected to pressing. In this event, the above mentioned water content of higher than 20% by weight is not preferable because the resultant tablet becomes sponge like. With the silicon dioxide of higher than 2% by weight, the compressing shapability will be deteriorated.

A plain tablet containing the anion exchange resin is coated with a coating solution containing 10–30 cSt (centistokes; defined in Japanese Pharmacopoeia as a viscosity of a 2%-aqueous solution at 20° C.) of hydroxypropylmethylcellulose (hereinafter, also referred to as a high-viscosity hydroxypropylmethylcellulose) by using a coater such as a High-Coater HCT-30 (available from Freund Industrial Co., Ltd.) under conditions of, for example, 80°–90° C. in suction temperature and 5–10 g/min. in a spray rate.

In the present invention, water may be used as a solvent of the coating solution. For coatings with water used as the solvent, the plain tablet will be swollen during coating if the plain tablet has a water content of lower than 14% based on the weight of the anion exchange resin, which causes rupture of the coating film. Accordingly, as mentioned above, the plain tablet is required to have a water content of not lower than 14% to achieve the coating using water as the solvent.

In the present invention, a solid component may be added to the coating solution depending on applications thereof. The solid component may be, for example, titanium oxide, talc, low-substituted hydroxypropylcellulose, ethylcellulose, or pigments. In this event, the strength of the coating layer can be improved when the amount of the solid component(s) is not more than 50% by weight based on the weight of hydroxypropylmethylcellulose. With the solid component(s) of more than 50% the stability to the humidity of the coated tablet is significantly lowered.

The coating solution may contain, along with the above mentioned high-viscosity hydroxypropylmethylcellulose, low-viscosity hydroxypropylmethylcellulose, and celluloses such as hydroxypropylcellulose and methylcellulose that are pH independent and is water-soluble, which may be used alone or as a combination.

Further, water-insoluble ethylcellulose or a small amount of wax may be added to the water-soluble cellulose to control a disintegration time of the tablet or to improve a moisture resistant effect.

With the hydroxypropylcellulose or the low-viscosity hydroxypropylmethylcellulose used in combination with the high-viscosity hydroxypropylmethylcellulose, the stability of the coating layer will be lowered significantly when they are mixed with each other. With respect to this, tablets are first undercoated with a coating solution consisting of, for example, hydroxypropylcellulose or the low-viscosity hydroxypropylmethylcellulose, on which a coating solution of the high-viscosity hydroxypropylmethylcellulose is overcoated. This permits production of stable tablets even in a moistening environment.

While not being limited to a specific value, the amount of the coating layer is preferably 1–5% by weight based on the weight of the tablets containing the anion exchange resin for a single use of the high-viscosity hydroxypropylmethylcellulose.

The orally administrable cholesterol lowering agent so obtained according to the present invention has a coating layer of approximately 30–160 μm thick, and preferably approximately 60–120 μm thick. With the double coating, the amount of the coating layer is preferably 1–4% by weight for the undercoating, and is 0.5–2% by weight for the overcoating. The orally administrable cholesterol lowering agent according to the present invention is formed into tablets, and preferably into capsule-shaped tablets.

A dosage of the present orally administrable cholesterol lowering agent may be 1 to 10 g daily for adults, preferably 1.5 to 4 g, because of a higher activity as compared with the prior art product, and the agent may usually be administered in 1 to 3 divided forms daily.

Now, the present invention is described more in detail in conjunction with a set of specific examples. The present invention is, however, not limited to those specific examples as long as it is within the scope thereof.

EXAMPLE 1

500 g of HCI-196 (water content 5%) is placed in a speed kneader (available from Okada Seiko Co., Ltd.), to which 58.7 g of the 5%-aqueous solution of hydroxypropylcellulose is added and blended. 2.38 g of hydrated silicon dioxide is added thereto and mixed therewith while stirring further. After picked up, the mixture is granulated by using a speed mill (available from Okada Seiko Co., Ltd.), to which 1.9 g of a hydrogenated oil is added and mixed therewith. Thereafter, the mixture is subjected to pressing. The resultant plain tablet contains 17% by weight of water and 0.5% by weight of the hydrated silicon dioxide based on the weight of the anion exchange resin.

The resultant tablet was coated by using the High-Coater HCT-30 (available from Freund industrial Co., Ltd.) under the conditions of the suction temperature of 80° C. and the spray rate of 5 g/min. to produce an orally administrable cholesterol lowering agent. The coating solution of the following composition was prepared by dissolving hydroxypropylmethylcellulose (15 cSt) in water, to which titanium oxide, talc, and polyethylene glycol were added and mixed therewith. The mixture was passed through a sieve of 80 mesh and was then used for coating. The coating amount was 2.5% by weight based on the weight of the plain tablets. The coating layer was approximately 90 μm thick.

| Coating Solution Composition | | |
|---|---|---|
| Hydroxypropylmethylcellulose | 4.0 | wt. % |
| Titanium Oxide | 0.5 | |
| Talc | 0.5 | |
| Polyethylene Glycol | 0.8 | |
| Purified Water | 94.2 | |
| Total | 100.0 | wt. % |

EXAMPLE 2

The plain tablets obtained in the same manner as in Example 1 were undercoated with a solution having the following composition, and was then overcoated with a solution having the following composition to prepare an orally administrable cholesterol lowering agent. The coating was made under the same condition as in Example 1 by using the High-Coater HCT-30. The amount of the coating layer was 2.0% by weight for the undercoating and 1.0% by weight for the overcoating, both based on the weight of the plain tablets. The coating layer was approximately 110 μm thick.

| Undercoating Solution Composition | | |
|---|---|---|
| Hydroxypropylcellulose | 10.0 | wt. % |
| Titanium Oxide | 1.5 | |
| Talc | 1.5 | |
| Polyethylene Glycol | 2.0 | |
| Purified Water | 85.0 | |
| Total | 100.0 | wt. % |
| Overcoating Solution Composition | | |
| Hydroxypropylmethylcellulose | 4.0 | wt. % |
| Titanium Oxide | 0.5 | |
| Talc | 0.5 | |
| Polyethylene Glycol | 0.8 | |
| Purified Water | 94.2 | |
| Total | 100.0 | wt. % |

EXAMPLE 3

A relation between the amount of silicon dioxide added and the degree of hardness of the tablets was determined with the amount of the silicon dioxide in the plain tablet varied in a range from 0.1% to 2.0% by weight based on the weight of the anion exchange resin (MCI-196) through the above mentioned prescription. The degree of hardness of the tablets was measured by using a Monsand durometer under a compressing pressure of 700 kg. The result is shown in FIG. 1. It is apparent that the silicon dioxide of not more than 2.0% by weight results in the superior compressing shapability.

| Tablet Prescription | |
|---|---|
| Anion Exchange Resin | 500 mg |
| Purified Water | 85 |
| Silicon Dioxide | 0–10.0 |
| Hydrogenated Castor Oil | 2.0 |

| -continued | |
|---|---|
| Tablet Prescription | |
| | 587–597 mg |

COMPARATIVE EXAMPLE 1

Example 1 was repeated to prepare plain tablets except that the amount of the 5%-aqueous solution of hydroxypropylcellulose in the plain tablet was 38.7 g (the resultant plain tablets contained 13% by weight of water based on the weight of the anion exchange resin), which was coated in the same manner as in Example 1. As a result, the coating film was ruptured during coating and no coated tablet was obtained.

COMPARATIVE EXAMPLE 2

Example 1 was repeated to prepare an orally administrable cholesterol lowering agent except that the composition of the coating solution was changed as follows (hydroxypropylcellulose was used in place of hydroxypropylmethylcellulose).

| Coating Solution Composition | | |
|---|---|---|
| Hydroxypropylcellulose | 10.0 | wt. % |
| Titanium Oxide | 1.5 | |
| Talc | 1.5 | |
| Polyethylene Glycol | 2.0 | |
| Purified Water | 85.0 | |
| Total | 100.0 | wt. % |

COMPARATIVE EXAMPLE 3

Example 1 was repeated to prepare an orally administrable cholesterol lowering agent except that the composition of the coating solution was changed as follows (an amount of the solid components of titanium oxide and talc was 55%).

| Coating Solution Composition | | |
|---|---|---|
| Hydroxypropylmethylcellulose | 4.0 | wt. % |
| Titanium Oxide | 1.2 | |
| Talc | 1.0 | |
| Polyethylene Glycol | 0.8 | |
| Purified Water | 93.0 | |
| Total | 100.0 | wt. % |

TEST EXAMPLE 1

A stabilization test was performed in a moistening environment (40° C., 75% humidity, and opened bottle) by using the orally administrable cholesterol lowering agents obtained in Examples 1 and 2 and Comparative Examples 2 and 3. It is apparent from the following results that the orally administrable cholesterol lowering agent of the present invention is stable even in a moistening environment and has fluidity not to be deteriorated.

| | 1 day | | 7 days | | 14 days | |
|---|---|---|---|---|---|---|
| | Appearance | Fluidity | Appearance | Fluidity | Appearance | Fluidity |
| Example 1 | o | o | o | o | o | o |
| Example 2 | o | o | o | o | o | o |
| Comparative Example | o | x | o | x | o | x |

-continued

| | 1 day | | 7 days | | 14 days | |
|---|---|---|---|---|---|---|
| | Appearance | Fluidity | Appearance | Fluidity | Appearance | Fluidity |
| 2 Comparative Example 3 | Part of Film Rupture | o | Most of Film Rupture | o | All Film Rupture | o | o: satisfactory (without change)
x: fluidity down

EXAMPLE 4

Example 1 was repeated to prepare an orally administrable cholesterol lowering agent (tablet) except that 60.0 g of a 7.1%-aqueous solution of hydroxypropylcellulose was used in place of 58.7 g of the 5%-aqueous solution of hydroxypropylcellulose and that the coating amount was 2.7% by weight rather than 2.5% by weight. Equivalence of this orally administrable cholesterol lowering agent (tablet), MCI-196 (bulk substance), and HCI-196 (granules) according to a method in Reference Example below was determined with rabbit models fed a cholesterol diet.

Experiment was made with male New Zealand white rabbits (aged 10–12 weeks) weighing 2.2–3.2 kg. Rabbits were assigned to five groups, each having 5 to 9 rabbits.

During preliminary feeding, the rabbits were fed a cholesterol diet (rabbit feed containing 0.5% cholesterol available from Oriental Yeast Co., Ltd.) for 5 days to obtain rabbits suffering from hyperlipemia. Five (5) rabbits in a group A were further fed the cholesterol diet and 10 ml isotonic sodium chloride solution while nine (9) rabbits in a group B were fed the cholesterol diet and the bulk substance (500 mg dose per one rabbit) suspended in 10 ml isotonic sodium chloride solution. Seven (7) rabbits in a group C were fed the cholesterol diet and the granules (500 mg dose per one rabbit) suspended in 10 ml isotonic sodium chloride solution. Eight (8) rabbits in a group D were fed the cholesterol diet, the tablets (two 250 mg-tablets dose per one rabbit), and 10 ml isotonic sodium chloride solution. The rabbits were forced to administer the bulk substance, the granules and the tablets orally once a day.

Figure 2:
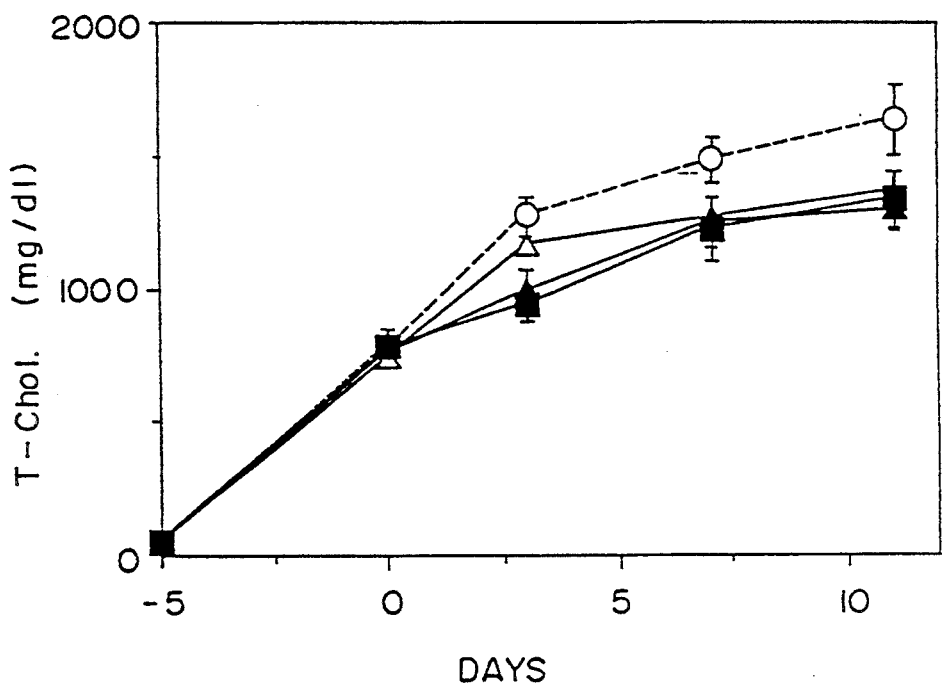
FIG. 2 illustrates biological activities of an orally administrable cholesterol lowering agent (tablet), a bulk substance, and granules in Example 4.

Blood samples were collected from the auricular vein of the rabbits after 3 hours of each administration of the drugs on the initial day of cholesterol diet feeding, and 3 days, 7 days and 11 days after the initial day. The total cholesterol levels in plasma obtained through centrifugal separation were determined quantitatively by using a cholesterol test Wako Kit available from Wako Pure Chemical Industries Co., Ltd. The results are given in FIG. 2. In the figures, symbols O, ▲, △, and ■ and represent results for the groups A, B, C, and D, respectively. FIG. 2 reveals that the orally administrable cholesterol lowering agent (tablets) according to the present invention has the equivalent biological activity to the case of administration in the form of the bulk substance or the granules.

EXAMPLE 5

Bile Acid Adsorption Test

Tablets (one tablet of 1 g and two tablets of 500 mg) and granules (1 g) of the orally administrable cholesterol lowering agent according to the present invention obtained in the same manner as in Example 4 were placed in 1000 ml of a 6 mM-aqueous solution of sodium cholate kept at 37°±0.5° C. The solution was sampled with time to measure a concentration of the sodium cholate.

The device used was an elusion test method (Second Method) defined in Japanese Pharmacopoeia made at a rotation speed of 50 rpm. A percentage of adsorption of the sodium cholate was calculated by using, as a reference 100%, an amount adsorbed when the bulk substance of MCI-196 is placed in 1000 ml of the 60 mM-aqueous solution of sodium cholate.

Figure 3:
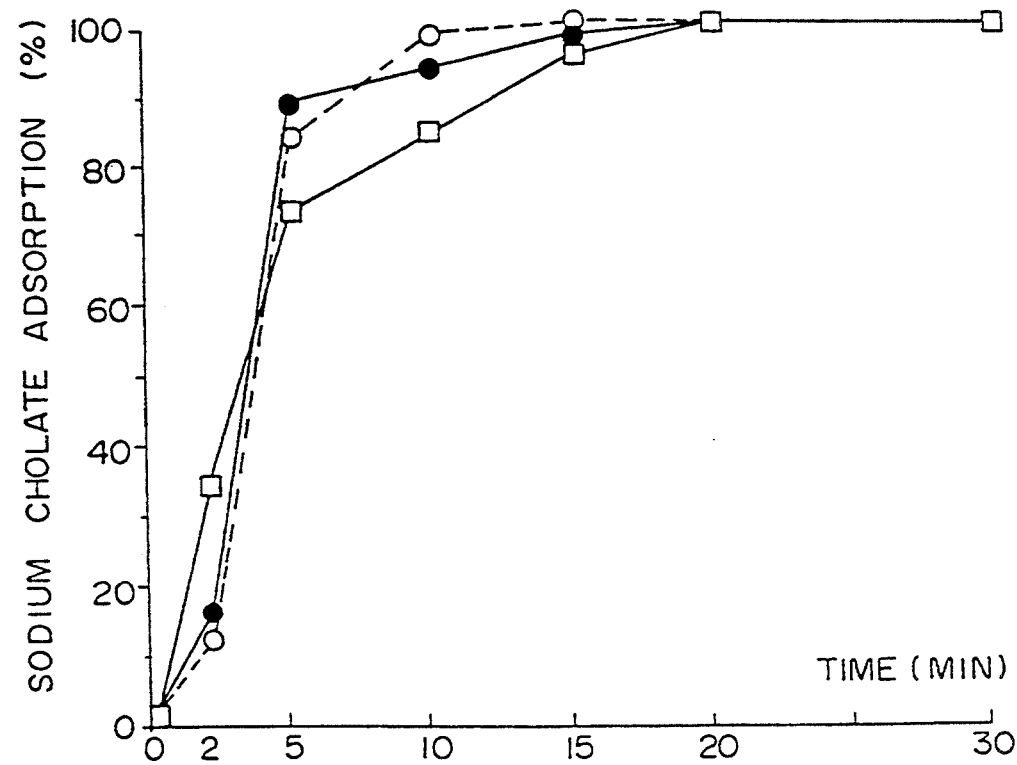
FIG. 3 illustrates the results of an adsorption test on an orally administrable cholesterol lowering agent (tablet), and granules in Example 5.

The results are given in FIG. 3, in which O, ●, and ■ represent the results for one tablet of 1 g, two tablets of 500 mg, and the granules of 1 g. The results show that the orally administrable cholesterol lowering agent (tablets) according to the present invention exhibits similar effects to those obtained with the granules in the bile acid adsorption test.

REFERENCE EXAMPLE

Method of Preparing Granules 10 kg of MIC-196 and 1.20 kg of hydroxypropylcellulose are placed in a vertical granulator (available from Powrex) and mixed with each other. Further, 530 g of glyceryl monostearate is heat dissolved in ethanol and mixed therewith, which is then subjected to extrusion granulation. The resultant compound is dried and then granulated by using a speed mill (OKada Seiko Co., Ltd.), following which the granules are screened. 8210 g of plain granules (plain granules are those in a range between 12 mesh and 42 mesh) are blended in SPIR-A-FLOW (Freund Industrial Co., Ltd.) and are coated with a solution obtained by heat dissolving 750 g of glyceryl monostearate and 187 g of ethylcellulose in ethanol. Subsequently, the granules are coated with a solution obtained by dissolving 47 g of hydroxypropylcellulose in ethanol, in which 19 g of sodium lauryl sulfate and 75 g of titanium oxide are suspended. The coated granules are screened to pick up those in the range between 12 mesh and 42 mesh (the granules in the range between 12 mesh and 42 mesh are used as the coated granules). Granules are obtained by adding and mixing 0.5% of calcium stearate based on the weight of the coated granules to and with the coated granules.

According to the present invention, there is provided an orally administrable cholesterol lowering agent which is superior in easiness of swallowing, compressing shapability, stability in a moistening environment, and fluidity.

What is claimed is:

1. An orally administrable cholesterol lowering agent obtained by coating with hydroxypropylmethylcellulose, plain tablets containing an anion exchange resin as an active component and containing 14–20% by weight of water and not more than 2% by weight of silicon dioxide based on the weight of the anion exchange resin.

2. An orally administrable cholesterol lowering agent of claim 1, wherein the anion exchange resin is 2-methytimidazole-epichlorohydrin copolymer.

3. An orally administrable cholesterol lowering agent of claim 1, wherein the thickness of the coating layer is from 30 μm to 160 μm.

4. An orally administrable cholesterol lowering agent of claim 1, wherein the orally administrable cholesterol lowering agent is in the form of a capsule-shaped tablet.

5. An orally administrable cholesterol lowering agent obtained by coating the plain tablet of the orally administrable cholesterol lowering agent of claim 1 with an aqueous solution of 10–30 cSt of hydroxypropylmethylcellulose.

6. An orally administrable cholesterol lowering agent of claim 5, wherein the aqueous solution of hydroxypropylmethylcellulose contains not more than 50% by weight of a solid component.

7. An orally administrable cholesterol lowering agent of claim 2, wherein the thickness of the coating layer is from 30 μm to 160 μm.

8. An orally administrable cholesterol lowering agent of claim 2, wherein the orally administrable cholesterol lowering agent is in the form of a capsule-shaped tablet.

9. An orally administrable cholesterol lowering agent of claim 3, wherein the orally administrable cholesterol lowering agent is in the form of a capsule-shaped tablet.

10. An orally administrable cholesterol lowering agent of claim 7, wherein the orally administrable cholesterol lowering agent is in the form of a capsule-shaped tablet.

11. A method of preparing an orally administrable cholesterol lowering agent comprising the steps of:
 (1) adding to an anion exchange resin 14–20% by weight of water based on the weight of the anion exchange resin while mixing, and then adding to the anion exchange resin not more than 2% by weight of silicon dioxide based on the weight of the anion exchange resin while mixing, and then pressing the mixture into plain tablets; and
 (2) coating the plain tablets with a coating solution which is an aqueous solution of 10–30 cSt of hydroxypropylmethylcellulose.

12. A method of preparing an orally administrable cholesterol lowering agent of claim 11, wherein the weight of the coating solution is 1–5% by weight based on the weight of the plain tablets.

13. A method of preparing an orally administrable cholesterol lowering agent of claim 12, wherein the coating solution contains not more than 50% by weight of a solid component based on the weight of hydroxypropylmethylcellulose.

* * * * *